United States Patent [19]

Dahms

[11] 4,019,861
[45] Apr. 26, 1977

[54] METHOD AND APPARATUS FOR MEASUREMENT OF $CO_2$ AND CHLORIDE IN BODY FLUIDS

[75] Inventor: Harald Dahms, Ossining, N.Y.

[73] Assignee: Corning Glass Works, Corning, N.Y.

[22] Filed: June 30, 1976

[21] Appl. No.: 701,164

[52] U.S. Cl. .......................... 23/230 B; 23/253 R; 204/1 T; 204/195 T
[51] Int. Cl.$^2$ ................ G01N 33/16; G01N 27/30; G01N 27/42
[58] Field of Search .................... 23/230 B, 253 R; 204/1 T, 195 T

[56] References Cited
UNITED STATES PATENTS

| | | | |
|---|---|---|---|
| 3,874,850 | 4/1975 | Sorensen et al. | 23/253 X |
| 3,964,864 | 6/1976 | Dahms | 23/253 X |

*Primary Examiner*—R.E. Serwin

[57] ABSTRACT

An improved apparatus and method for detecting $CO_2$ and $Cl^-$ in body fluids, such as whole blood, blood serum and plasma, etc. A reagent and a known amount of the sample to be tested react in a vessel to release $CO_2$ into a gas space. The released gas is then displaced to a detector where its concentration in a substantially stationary gas sample is measured. After both $CO_2$ and $Cl^-$ have been measured, the mixture of sample, reagent, and gas is then drained from the vessel and from the detector and a reverse flow of excess flushing fluid (gas) is moved through the detector and the vessel to flush the apparatus so that another measurement can begin. After each measurement, the instrument is zeroed. In the practice of the present invention, the zeroing operation is more accurate when the flushing gas is equilibrated with the reagent solution, i.e., when the air used for flushing has picked up some of the vapors of the reagent solution. In further aspects of this invention, electrodes are provided in the reaction vessel for coulometric titration of chloride. An improved electrode assembly is provided for this. Heating means is provided to heat the gas flowing from the reaction vessel to the detector to insure the accuracy of the measurement results.

39 Claims, 5 Drawing Figures

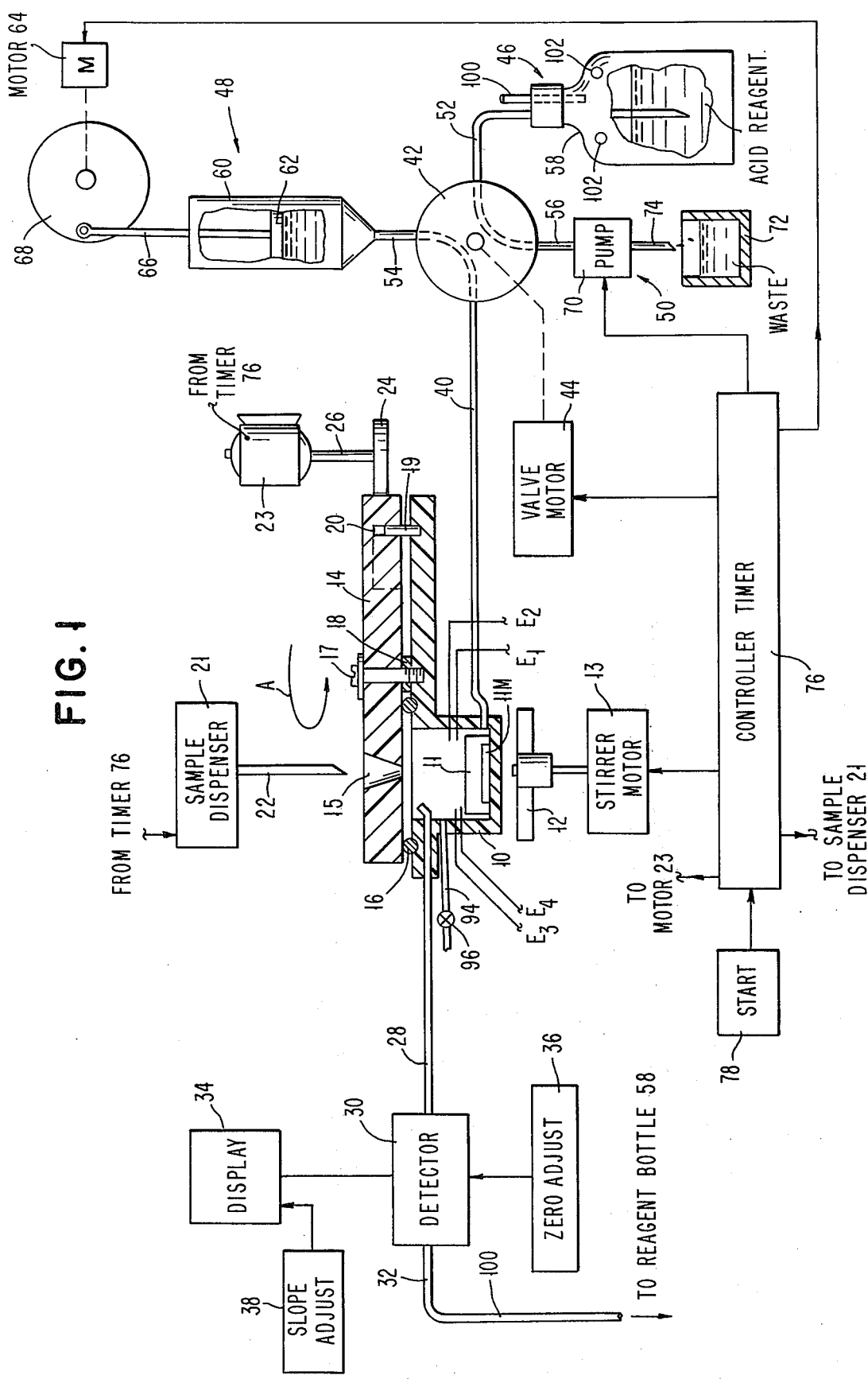

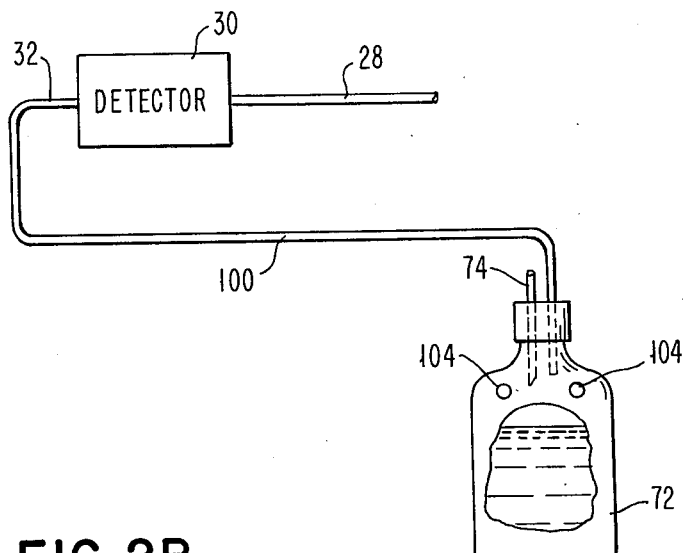
FIG. 2A
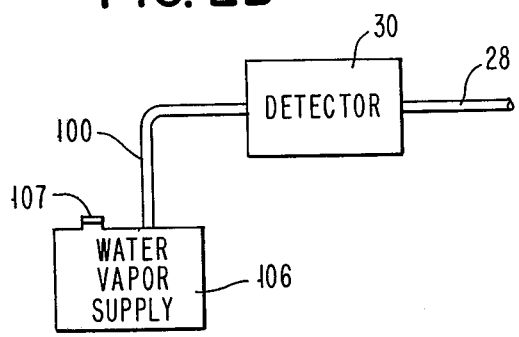
FIG. 2B
FIG. 3
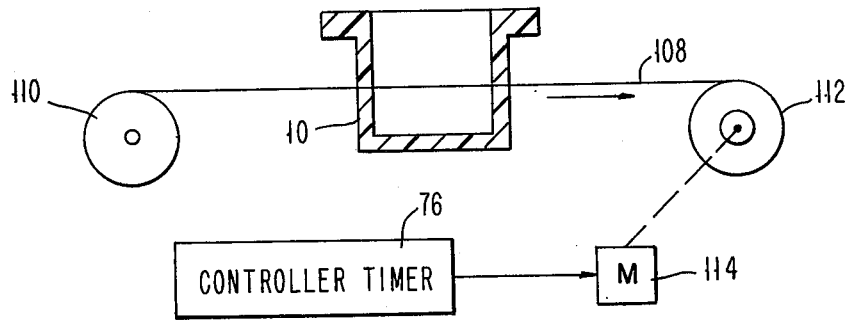
FIG. 4
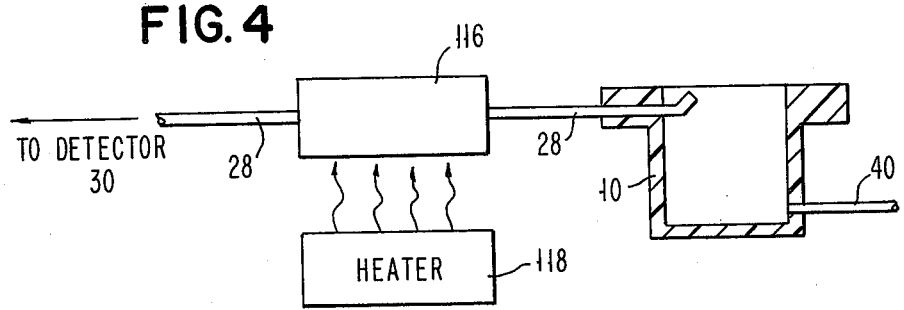

METHOD AND APPARATUS FOR MEASUREMENT OF $CO_2$ AND CHLORIDE IN BODY FLUIDS

BACKGROUND OF THE INVENTION

1. Field of the Invention

This invention relates to improved techniques for measurement of species in body fluids, and more particularly to improved methods and apparatus for measurement of $CO_2$ and $Cl^-$ in body fluids.

2. Description of the Prior Art

The determination of blood gases is important for clinical analysis. In particular, the determination of carbon dioxide ($CO_2$) and chloride content in whole blood and blood serum are among the most frequently performed analyses in a clinical laboratory. Due to the great importance of these analyses, a number of techniques have been developed and are presently being used to determine concentrations of these species.

Of these techniques, the one described in copending application Ser. No. 524,793, now U.S. Pat. No. 3,964,864 describes a particularly advantageous technique for determining concentrations of these species in blood samples. An instrument using that technique has been manufactured and sold by Ericsen Instruments, Ossining, N.Y., under the model number Ericsen E-100 Carbon Dioxide Analyzer.

The measurement apparatus described in aforementioned U.S. Pat. No. 3,964,864 uses an equilibrated, substantially stationary system to obtain more accurate results, and can be used for the analysis of very small blood samples. The apparatus is automatically cleaned after each measurement, thus insuring good accuracy and rapid measurement. Further, the blood gas is measured by the detector at essentially the same composition as that originally established in the vessel, thereby insuring increased accuracy.

In the instrument described in U.S. Pat, No. 3,964,864 $CO_2$ and chlorides can be measured in body fluids. A known amount of sample, such as blood serum, plasma, or whole blood, is introduced into a reaction vessel. The vessel is then closed and the sample is stirred with a small amount of reagent present so that the gas species to be detected will be released from the sample and the gas space in the vessel will become equilibrated with the released species. The release of the gas species into the gas space of the vessel is at atmospheric pressure. After the gas space has been equilibrated with the released gas, the released gas is transferred to a detector. Generally, this transfer occurs by introducing a displacement liquid, such as additional reagent, into the reaction vessel in order to push the equilibrated gas to the detector. The detector measures the concentration of a substantially stationary sample of the released gas.

After all measurements are made, the mixture of sample and reagent in the closed vessel is then drained from the vessel and excess flushing fluid (such as air) is passed through the detector and through the vessel in order to flush the apparatus prior to making another measurement. The volume of fluid flushed through the entire apparatus is significantly greater than the volume of the closed vessel, thereby insuring that proper cleansing will occur. The flow of the flushing fluid through the apparatus is preferably in a reverse direction to the direction of movement of the released gas to the detector.

In the practice of the invention described in aforementioned U.S. Pat. No. 3,964,864, it has been found that under certain operating conditions the measurement apparatus may show a reading different from zero even if the sample content of the released gas is zero. That is, when the instrument is zeroed after each measurement, it has been found that the zero calibration does not always provide an accurate zeroing of the instrument. Through laboratory studies, it has been determined that this problem arises because the detector sees a slightly different gas composition when it is measuring the released gas than when it is exposed to the flushing fluid during cleansing of the instrument. This difference may become significant if the air in the atmosphere is especially dry (low relative humidity) and/or the temperature of the atmosphere is extremely high.

Thus, it is a primary object of the present invention to provide a technique for correcting for the possibility of error when zeroing the aforementioned instrument after each measurement is made.

It is a further object of the present invention to provide improved methods and structure for zeroing the aforementioned instrument after each measurement analysis, using a technique which is very simple and inexpensive, and which provides accurate zeroing results.

In U.S. Pat. No. 3,964,864, the disclosed instrument showed structure which would allow measurement of chlorides in the body fluid sample. In particular, the reagent vessel was modified to provide optical equipment used to make the chloride measurement. A light source of proper wavelength and light guides are provided for passing light through the vessel and then to a detector, which is a conventional colorimetric or spectrophotometric apparatus for determining chloride content.

In the improved detector and methods described herein, other means for measurement of chlorides is provided. These means are particularly simple and measure chlorides by coulometric titration which is described for example, by E. Cotlove in "Standard Methods of Clinical Chemistry", Volume 3, pp. 81–92, published by Academic Press, New York, 1961. In that type of coulometric measurement a silver generator electrode is used which is consumed during the reaction to release silver ions ($Ag^{115}$). This means that the electrode has to be replaced from time to time which is a disadvantage of that type of chloride measurement.

Accordingly, in the practice of the present invention, it is another primary object to provide an improved means for chloride measurement in body fluid samples.

It is another object of the present invention to provide an improved apparatus for measurement of chloride in body fluid samples which is simple and reasonable, and which continually compensates for deterioration of the electrodes used in making these measurements.

In the practice of the present invention, it has been found that the improved apparatus for determining species such as $CO_2$ and $Cl^-$ in body fluid samples requires additional refinement in order to provide accurate results. In particular, heating of the gas transferred to the detector has been found to yield improved results, since heating eliminates trace amounts of impurity gases.

Accordingly, it is another object of the present invention to provide an improved apparatus and method for measuring $CO_2$ and $Cl^-$ in body fluid samples, which is simple and inexpensive and which yields very accurate results.

It is another object of the present invention to provide an apparatus and method for measuring $CO_2$ and $Cl^-$ in body fluid samples by a technique which eliminates the adverse affect of additional species during the determination of $CO_2$ and $Cl^-$.

It will be appreciated that the present technique for measuring $CO_2$ and chlorides in very small samples of body fluids provides a simple, quick, and reliable measurement of a substantially stationary sample, as opposed to a flowing gas sample. The species to be measured is released at substantially atmospheric pressure, rather than being released into a vacuum. In the practice of this invention, no complicated apparatus is required for separation of various gas constituents in the body fluid sample, and no additional reagents have to be added in order to separate $CO_2$ from other gases which may affect the accuracy of the $CO_2$ measurements.

BRIEF SUMMARY OF THE INVENTION

Reference is again made to U.S. Pat. No. 3,964,864 whose teaching is incorporated herein by reference to that patent. That is, the basic method and apparatus described therein are used here, with the modifications referred to in the introduction.

Typically, a known amount of the body fluid sample is introduced into a vessel. The vessel is then closed and the sample is stirred with a small amount of reagent present so that $CO_2$ is released from the sample and the gas space in the vessel is equilibrated with the released species. The release of $CO_2$ into the gas space is at atmospheric pressure.

After the gas space has been equilibrated with the released gas, a displacement fluid (such as the reagent) is introduced into the vessel, and pushes the equilibrated gas into a detector connected to the gas space of the closed vessel. After the displacement of some of the gas from the gas space into the detector, the detector measures the concentration of a substantially stationary sample of the released gas species. The measurement is conveniently displayed for the operator to view.

After the measurement is made, the mixture of sample and reagent in the closed vessel is then drained from the vessel and excess flushing fluid (such as air) is passed through the detector and through the vessel in order to flush the apparatus prior to making another measurement. The flushing fluid flows through the apparatus in a direction reverse to the direction of movement of the released gas to the detector.

Added to the apparatus of that patent is a means for insuring that the instrument will properly zero after each measurement. This means insures that the flushing fluid is equilibrated with a reagent solution. The detector will be exposed to the same gas composition when it is being used for a measurement as when it is being flushed after the measurement.

The structure used to provide an equilibration between the flushing fluid and the released gas during measurement is conveniently provided by a tubing which connects either the gas space of the reagent bottle or the gas space of the waste bottle to the detector. Vent holes are provided in either the reagent bottle or the waste bottle when the gas space of either of these bottles is connected to the detector. The purpose of the vent holes is to avoid accumulation of the released $CO_2$. Another technique for achieving this equilibration is to provide a source of the vapors in the gas space of the waste bottle or the reagent bottle, where the source of the vapors is connected to the detector and is used during the flushing operation.

The basic apparatus of U.S. Pat. No. 3,964,864 is also modified to provide coulometric titration of chlorides in the body fluid sample. A plurality of electrodes is present in the reaction vessel which are connected to the appropriate sources as described in the reference of E. Cotlove, cited above. A disadvantage of the present coulometric chloride analysis is the fact that the silver electrode has to be replaced and cleaned. Typically, the operator has to replace the generator electrode after about 100 analyses. In addition, he has to clean the other electrodes after one or more days of operation. After the replacement and cleaning operations, the new electrodes and the cleaned electrodes have to be "conditioned", i.e., the operator has to perform one or more test titrations before he is ready to again run actual samples. It has also been found that the results of such measurements depend on the age and condition of the electrodes. Present results are therefore not highly accurate. The present invention eliminates these disadvantages of coulometric titration. In order to provide a more satisfactory coulometric titration, one or more of the electrodes is continually advanced into the reaction vessel so that new portions of the electrode wire will be present during each measurement. This solves the problem of deterioration of the electrodes during the titration.

The conventional tubing which connects the gas space of the reaction vessel and the detector is modified to provide heating of the gas which is released into the detector. As an example, the normally used plastic tubing connecting the reaction vessel and the detector includes a stainless steel section which is heated to provide an elevated temperature region through which the released gas passes as it goes from the reaction vessel to the detector. This eliminates impurities which would interfere with the accuracy of $CO_2$ measurement.

These and other objects will be apparent from the following more particular description of the preferred embodiments.

BRIEF DESCRIPTION OF THE DRAWINGS

FIG. 1 shows an apparatus for detection of $CO_2$ and $Cl^-$ in body fluids such as whole blood, blood serum, and blood plasma. This apparatus includes means for properly zeroing the instrument after each measurement and means for coulometrically determining the amount of chlorides present in the sample of body fluid to be analyzed.

FIG. 2A shows a portion of the apparatus of FIG. 1, in which the means for properly zeroing the instrument includes a tube connection between the detector and the gas space of the waste bottle.

FIG. 2B shows another embodiment for properly zeroing the instrument, using a source of reagent vapors attached to the detector.

FIG. 3 shows a spool assembly for continually advancing an electrode through the reaction vessel.

FIG. 4 shows a portion of the apparatus of FIG. 1, in which the tubing line 28 connecting the reaction vessel and the detector is modified to provide a high temperature zone through which the released gas from the reaction vessel passes on its way to the detector.

DETAILED DESCRIPTION OF THE PREFERRED EMBODIMENTS

FIG. 1

FIG. 1 shows the basic apparatus of U.S. Pat. No. 3,964,864. Additionally, means are provided for coulometrically titrating the body fluid sample to determine the concentration of chloride therein and for properly zeroing the instrument after each measurement. The following description will explain the basic apparatus of U.S. Pat. No. 3,964,864.

A vessel 10 is provided which can be closed and in which the sample is placed together with a reagent such as acid, which reacts with the sample to release gas ($CO_2$) from the sample. As mentioned, the sample is comprised of a body fluid, such as blood serum, whole blood, blood plasma, etc. as typical examples. In the rest of the specification, the sample will be generally indicated as blood or body fluid in order to facilitate the description. Located in vessel 10 is a stirring bar 11 which has a magnetic portion 11M that is driven by magnet 12 which is in turn connected to stirrer motor 13. Of course, a directly driven stirrer can also be used.

Stirrer 11 is used to enhance release of the gas to be detected in the gas space of vessel 10. It does this by increasing the interface area of the sample/reagent solution and the gas space in vessel 10.

A stirrer 11 such as that shown in FIG. 1 can be used to create a thin film of the sample/reagent solution along the walls of vessel 10. For instance, if the stirrer has a length $l$ close to the inner diameter $d$ of vessel 10, a thin film of the solution will be formed along the walls of vessel 10. For $d - l < 1$ mm, a thin film of thickness $< 1$ mm will be formed. For a vessel having a height of 15 mm and volume about 2 ml, the stirrer can be about 12 mm high and about 10 mm wide. By using a stirrer such as this, more than 95% of the gas to be detected will be released in less than 20 seconds, in contrast with previous techniques requiring stirring times of about one minute.

Additionally, stirrer 11 can have any number of blades, rather than being two-bladed as shown in FIG. 1. This will further increase the solution/gas space interface area. As can be appreciated, this invention provides a thin film of solution by using a large stirrer and a small volume of sample.

Reaction vessel 10 has associated therewith a moveable cover 14, having an opening 15 therein. Cover 14 rests against O-ring 16 and exerts pressure thereon to close the top opening of vessel 10. Opening 15 can be brought into and out of communication with the top opening of vessel 10 depending on the rotation of cover 14. That is, cover 14 can be rotated in reverse directions in accordance with arrow A in order to provide access to the interior of vessel 10.

Vessel 10 and cover 14 are generally comprised of materials which are chemically inert and which will not influence the reaction of the sample and the reagent. Suitable materials are plastics and glasses. In FIG. 1, cover 14 is held in contact with O-ring 16 by an alignment and fastening means 17, which is conveniently a screw which is surrounded by a bushing 18. A pin 19, located in the top surface of vessel 10, travels in a guide 20 in cover 14 in order to limit the motion of cover 14 which is used to bring opening 15 into and out of communication with the top opening of vessel 10.

During operation, the filling hole 15 is over vessel 10 so that a sample can be placed in vessel 10. The sample can be placed in vessel 10 by an operator using a suitable instrument such as a pipette, or placement can be done automatically. An automatic operation will typically use a sample dispenser 21 which may receive samples from a turntable (not shown). The sample is then discharged through tubing 22 in order to enter vessel 10. All of this operation can be done automatically under control of separate circuitry.

Movement of the cover plate 14 to bring filling hole 15 into and out of contact with the top vessel 10 can be done by a driving means comprising a motor 23 and a drive wheel 24 which is connected to the motor via drive shaft 26. The operation can also be done automatically and synchronized with the operation of the sample dispenser 21, through the use of appropriate control circuitry.

The volume of vessel 10 is chosen in accordance with the typical amount of sample to be tested. For example, vessel 10 has a volume which is typically of the order of 1 ml. The volume of vessel 10 has to be larger than the combined volume of line 28 and detector 30 so that line 28 and detector 30 can be flushed when the equilibrated gas is transferred. Also, the volume of additional reagent injected to transfer the equilibrated gas is less than the volume of line 28 plus the volume of vessel 10, to prevent reagent from entering detector 30. Thus, the volume of the displacement reagent used to transfer gas to the detector is less than the volume of vessel 10 minus the volume of stirrer 11.

Thin tubing 28 connects vessel 10 with a detector 30. Detector 30 may be a thermal conductivity detector containing thermistors or hot wire filaments as is generally well known. Thermal conductivity detectors (also called katharometers) usually measure the heat loss through a gas from the prime heat source (filament or thermistor) into a cell block or heat sink. The detector elements or heat sources are organized in a Wheatstone Bridge permitting the imbalance resulting from the change in a sample gas to be read on a meter, etc. The detector elements may, for example, be thermistors or hot wires made of tungsten, tungsten alloys or other suitable materials. For a review of such detectors, reference is made to an article by A. E. Lawson et al, entitled "Thermal Conductivity Detectors in Gas Chromatography", which appeared in Gas Chromatography, Vol. 4, page 273 (1966). Depending upon the thermal conductivity of the gas in contact with the wire filament, the detector will provide an indication of the concentration of the gas in contact with the wire filament. These detectors are manufactured and sold by a number of companies, such as Beckman Instruments, Fullerton, Calif., Fisher Scientific, Pittsburgh, Pa., among others.

Detector 30 is provided with an output tubing vent 32, which is used for the flushing operation to be described later.

When the vessel 10 has a volume of about 1 ml, the thin tubing will typically have a volume of only about 0.1 ml or less. For these volume dimensions, the internal volume of detector 30 should preferably not be larger than about 0.1 – 0.2 ml.

Detector 30 is connected in a conventional bridge circuit to display 34 which indicates the amount of $CO_2$ being detected. The bridge circuit can also include a zero adjust circuit 36 and a slope adjust circuit 38 which is used for calibration purposes. Thus, a detection means for indicating the concentration of $CO_2$ in the sample is generally comprised of detector 30, display 34, zero adjust 36, and slope adjust 38.

Vessel 10 is also controllably connected to a means for putting a reagent into the vessel, a means for adding displacement fluid to the vessel to expel released gas into tubing 28, and a means for flushing the detector and vessel 10 after a sample analysis is made. These various means are generally connected to vessel 10 via tubing 40, through the action of a rotary valve 42. Valve 42 is driven by valve motor 44 which can be automatically controlled by appropriate timer circuitry, as will be described. The means for putting reagent into vessel 10 initially is generally designated 46, the means for adding displacement fluid to expel the released gas from vessel 10 is generally indicated by numeral 48, while the means for flushing the vessel 10 and detector 30 after an analysis is generally indicated by numeral 50.

Various lines are used to controllably connect these various means 46, 48 and 50 to tubing 40 which communicates with vessel 10. Rotary valve 42 can make and break connections to line 52 which goes to means 46, to line 54 which goes to means 48, and to line 56 which goes to means 50.

Reagent means 46 generally comprises a container 58 for storing the reagent used to react with the sample. For measurement of $CO_2$, this reagent is generally an acid such as a 1M aqueous solution of lactic acid, or the improved acid reagents described in Applicant's copending application Ser. No. 698,868 filed June 23, 1976.

The reagent adding means 48 is used to provide a small amount of displacement fluid (such as reagent) into vessel 10 in order to push released gas to the detector 30. Means 48 is typically comprised of a cylinder 60 having a movable piston 62 therein. The reagent used in the detection is also preferably present in cylinder 60. Piston 62 is driven by a motor 64 which is connected to shaft 66 via eccentric 68. Motor 64 can also be under control of an appropriate timing circuit to automate the actuation of means 48 at the proper time. While transfer of the gas mixture in the vessel gas space is preferably done by using a displacement fluid, other methods, such as pumping, can be used to accomplish the transfer.

Flushing means 50 is generally comprised of a pump 70 which removes reagent and sample from vessel 10 and also removes released gas from detector 30 and vessel 10 after a measurement has been made. The flushed material is released into waste container 72 via tubing 74. The operation of pump 70 can also be controllably activated by appropriate control circuitry. Additionally, means 50 moves a flushing fluid through the detector 30, tubing 28, and vessel 10, to cleanse these parts prior to each new measurement.

A controller timer 76 is actuated by start circuit 78 and is used to control the operation of stirrer motor 13, sample dispenser 21, drive motor 23, valve motor 44, motor 64, pump 70 and all valves. Timer 76 provides start signals to each of these components at the proper time to provide totally automatic operation in order to determine $CO_2$ content from a sample of body fluid placed in vessel 10. This automatic operation includes a flushing step which cleanses detector 30 and vessel 10 after each individual sample measurement is made, and which actuates the beginning of another sample measurement. Consequently, measurements numbering approximately 60 (or more) per hour can be made by this apparatus in contrast with prior art measurement speeds typically less than 10 measurements per hour.

The apparatus described thus far is the basic $CO_2$ analyzer of U.S. Pat. No. 3,964,864. In the present invention, a means for properly zero adjusting the instrument is provided. This structure insures that the vapor composition to which the detector is exposed during flushing is the same as the vapor composition to which it is exposed during the measurement phase of operation. Thus, the flushing fluid is equilibrated with the reagent solution by insuring that the air used for flushing has picked up some of the vapors of the reagent solution. For this purpose, tubing vent 32 is connected to a tubing 100 which picks up gases over the reagent contained in bottle 58. This structure insures that the zero condition approximates closely the measuring condition, since in both cases the flushing air is saturated with the vapor constituents of the reagent solution.

Vent holes 102 are provided in the sides of the bottle 58 to avoid accumulation of gaseous $CO_2$ in the gas space of reagent bottle 58. The size of the holes should be sufficient to allow $CO_2$ to escape. On the other hand, the holes should not be so big that the equilibrated gas is not retained. Two holes of one-quarter inch diameter proved to be suitable. Since the vent holes 102 allow essentially all of the $CO_2$ to escape, the flushing air (which is in contact with the liquid reagent) will be very similar to the gas mixture transferred to the detector during $CO_2$ measurement, except that $CO_2$ is not present in the flushing air.

As will be more apparent from FIGS. 2A and 2B, other apparatus can be used to equilibrate the flushing fluid with the released gas composition transferred to the detector during measurement. For instance, it is preferable to connect tubing 100 to the gas space of waste bottle 72 instead of to the gas space of the reagent bottle 58. Additionally, a source of the vapor constituents present during measurement can be directly connected to the detector. In this latter situation, a source of water vapor would work well, since the acid generally is an aqueous solution and the vapor over the reagent solution is mostly water vapor. Thus, a source of water vapor connected to the detector would insure that the flushing fluid is substantially the same as the released gas composition sent to the detector during the measurement phase of operation.

For the coulometric titration to determine chloride content, electrodes E1–E4 are shown in FIG. 1. These are wires which pass through reaction vessel 10 to the interior of this vessel. As is well known, two of these electrodes (such as E1 and E2) are connected to an indicator and are termed indicator electrodes. The other two electrodes (E3 and E4) are electrically connected in series and are termed the generator electrodes. Referring to the description of chloride titration given in E. Cotlove, referenced above, the chloride determination is as follows.

After $CO_2$ has been determined, there is acid solution and sample present in the reaction chamber 10. There is sufficient solution there to completely cover all four electrodes E1–E4. At this time, a constant current is passed through the two generator electrodes E3 and E4. This releases silver ions at a constant rate which combine with free chloride ions to form silver chloride, until an excess of free silver ions is generated. This excess of free silver ions gives rise to a current which is sensed by the indicator electrodes. Through proper calibration, the amount of chloride present in the body fluid sample is then known, as described by Cotlove.

FIGS. 3 and 4 will show further modifications to the apparatus of FIG. 1 which enable efficient chloride titration and accurate measurement of $CO_2$ and chlorides.

$CO_2$ Analysis Operation

The inject the sample of body fluid to be tested into vessel 10, cover 14 is moved so that opening 15 is over the top opening of the vessel 10. This sample can have very small volume, as for instance, 0.05 ml. Thus, pediatric samples can be easily analyzed. The sample to be analyzed is injected into vessel 10 by an operator or by automatic dispensing equipment 21. Vessel 10 is then closed by turning cover 14 to move opening 15 away from the top opening of the vessel. If the movement of cover 14 is under control of timer 76, a signal will be provided to motor 23 and to sample dispenser 21 to initiate this operation. Controller timer 76 then provides a signal to valve motor 44 which causes the rotary valve 42 to connect lines 40 and 52 so that acid reagent will be introduced into vessel 10. In most measurements, the small amount of strong acid remaining on the walls of vessel 10 from the previous measurement cycle will be sufficient for reaction with the blood sample in order to release $CO_2$. Thus, initial amounts of reagent may or may not be required from source 58.

The timer 76 starts stirrer motor 13 which mixes the sample and reagent in vessel 10, by means of stirrer bar 11. The sample and reagent react to release $CO_2$ into the gas space in vessel 10 which is thus equilibrated. After about 20–30 seconds, timer 76 actuates motor 44 which rotates the rotary valve 42 in order to cause lines 40 and 54 to communicate with one another. Motor 64 is then actuated to push acid reagent (displacement fluid) from cylinder 60 into vessel 10, through the action of piston 62. The volume of reagent pushed into vessel 10 by the movement of piston 62 is chosen such that vessel 10 is not completely filled in order to avoid contaminating the gas detector 30 with reagent. As an example, for a vessel volume of 1 ml a typical volume of reagent to be injected by piston 62 is 0.7 – 0.8 ml (if no reagent were initially put into vessel 10 for release of $CO_2$).

The injection of reagent into vessel 10 displaces the equilibrated gas volume from vessel 10 into detector 30. It is preferable that the flow of gas is essentially stopped before the measurement is made. Since the displacement liquid in cylinder 60 is only used to push equilibrated $CO_2$ into detector 30, it need not be the reagent used for release of $CO_2$. For instance, any substance which would not absorb $CO_2$ and which would not overpower the reagent in vessel 10 to adversely affect the next measurement is suitable. Aqueous solutions containing salt are examples. The signal produced by detector 30 is displayed by display 34 where it can be easily read by the operator. Controller timer 76 may be stopped at this time to allow the operator time to read and record the displayed signal and to permit him to set the slope adjustment circuit 38 when running a calibration sample. After these operations, timer 76 may be restarted. The timer actuates motor 44 so that lines 40 and 56 are now communicating with one another. Pump 70 is also actuated by timer 76 causing vessel 10 to be drained and also drawing an excess of fresh air into vessel 10. It is important that not only the liquid is drained from vessel 10, but also that all of vessel 10 is filled with fresh air (through detector 30) so that the $CO_2$ equilibrated air is removed from the system. The amount of excess air drawn through the detector and vessel 10 is sufficient to provide good drainage of these units. For instance, a volume of at least approximately five times the volume of vessel 10 is suitable.

Valve motor 44 then connects lines 52 and 54 in order to fill cylinder 60 with reagent by means of motor 64. The valve motor 44 then moves rotary valve 42 in order to connect lines 54 and 40. This pushes a samall amount of reagent into the lines so that line 40 is filled and possibly a small amount of reagent (for instance 0.05 ml) gets into vessel 10.

As noted, it has been found that the apparatus also works well without injection of reagent into vessel 10 via piston 62, since the small amount of strong acid remaining on the vessel walls from the previous cycle is generally sufficient for reaction with the next blood sample.

The apparatus is now ready for the next sample. Before injecting the next sample or before the timer 76 actuates sample dispenser 21, the operator may check the display 34 which should read zero and may also set zero adjust circuit 36 to obtain a zero reading.

In the practice of this invention, it has been found that equilibrium between the acidified sample and the gas space in vessel 10 is more efficient when detergent is added to the acid reagent. For example, a solution of 1M lactic acid containing 5% by volume of polyoxyethylene (20) sorbitan monooleate, a commercially available surfactant, can be used. However, the reagents described in aforementioned application Ser. No. 698,868 are preferable. These reagents are comprised of acids having pH less than 4 and vapor pressure not in excess of 10 mm Hg, together with additives.

Determination of Chloride Content

In preparation, the device of FIG. 1 is used to determine the $CO_2$ present in the sample of body fluid to be analyzed. The stirring time is typically shortened to about 10 seconds so that the $CO_2$ result appears 12 seconds after the start of the analysis. At this point in time the stirrer is again activated and the chloride titration is performed. As an example, a current of 20 milliamps is suitable. The solution in the reagent chamber after the $CO_2$ analysis is the electrolysis solution for the titration.

The reagent solution used in this example had the following composition: 0.1 N nitric acid, 1.8 M lactic acid and 0.8 grams per liter of polyvinyl alcohol. This reagent solution is suitable for both the release of $CO_2$ from the body fluid sample and for the coulometric titration of chlorides in the body fluid sample.

The actual titration is in accordance with the method of E. Cotlove, described above. There are now some modifications of the Cotlove chloride titration in use which may also be used in this invention. In the Cotlove method, the titration endpoint is measured amperometrically, i.e., the electrical current between the two indicator electrodes is measured. When the indicator electrical current rises due to the presence of free silver ions, the titration endpoint is reached.

In one modification, the titration endpoint is measured potentiometrically, i.e., the voltage between an indicator electrode and a reference electrode is measured and the titration endpoint is signaled by a change in that voltage. Also, the current passed for generating silver ions need not be constant. It may be higher in the beginning of the titration and lower when approaching the endpoint. Such modifications are well known in the art and may be employed in this invention. All such modifications still fall under the class of coulometric titration.

After the coulometric analysis is completed, the solution is drained from the reaction vessel and the detector, tubing 28, and reaction vessel are flushed with the flushing fluid as described. The apparatus is then ready for the next combined $CO_2$ and chloride analysis.

Although it is less preferable, it is also feasible to determine chlorides first and then to add some additional reagent solution to push the gaseous $CO_2$ to the detector.

During the chloride determination, the silver electrodes are consumed since some of them deliver $Ag^+$ ions. A technique for minimizing maintenance and for avoiding replacement of such electrodes will be described later with respect to FIG. 3.

For the combined $CO_2$/chloride instrument, tubing 28 included a section which could be heated to about 300°-800° C. Since the chloride determination may release impurities, heating a section of the tubing 28 prevents these impurities from getting to the detector in order to avoid interference with the $CO_2$ measurement.

FIG. 2A

This figure shows a portion of the apparatus of FIG. 1, except that the tubing 100 is connected to the gas space above the waste bottle 72, (which is shown as a closed vessel in this figure), rather than to the gas space of the reagent bottle 58. For reasons of simplicity, the entire apparatus of FIG. 1 is not repeated; rather, only the pertinent portions are shown.

As was indicated previously, tubing 100 serves to insure that the atmosphere seen by the detector 30 during the cleansing phase of operation is substantially the same as that seen by the detector 30 during the measuring phase of operation. The embodiment of FIG. 2A is preferred for ensuring that the constituents in the flushing fluid are similar to those in the gas sample seen by the detector during $CO_2$ measurement (except that $CO_2$ is not present in the flushing air). Further, a large supply of flushing air is provided by this technique, in which the liquid solution contacted by the flushing fluid is the mixture of the spent sample (having no $CO_2$ in it) and the reagent.

Thus, FIG. 2A shows the detector being connected to the gas space of the waste bottle 72 by tubing 100. Vent holes 104 are provided to the gas space of waste bottle 72, for the same reason that the vent ports 102 were provided in bottle 58.

FIG. 2B

This figure shows another embodiment for equilibrating the flushing fluid with the atmosphere seen by detector 30 during the measuring phase.

Since the gas space above the reagent in bottle 58 and above the waste solution 72 is largely water vapor, a source 106 of water vapor can be connected to tubing 32 via a (not shown) valve. Vent hole 107 serves the same purpose as does vent holes 102 and 104. Thus, the flushing fluid will have essentially the same relative humidity as the atmosphere seen by the detector 30 during the measuring phase.

FIG. 3

FIG. 3 shows a structure for continually advancing a silver electrode wire through the reaction chamber 10. The silver electrode wire 108 becomes consumed during the coulometric determination of $Cl^-$ since the wire delivers $Ag^+$ ions into solution during the analysis. In order to minimize maintenance and to avoid replacement of such electrodes, the silver wires 108 are arranged on spools 110 and 112. Spool 110 is an idle spool while spool 112 is a driven spool. Motor 114 is mechanically connected to the axis of spool 112 and causes spool 112 to advance in response to signals from the controller timer 76.

Thus, silver wire 108 is slowly pulled through reaction vessel 110 by the action of the small clock motor 114 whenever an analysis is performed. Alternatively, the wire may be advanced between analyses while being stationary during each individual analysis. As an example, a silver wire 0.050 inch in diameter was advanced 1/32 inch after every analysis. It should be understood that, rather than using the controller timer to trigger motor 114, other means can be provided for advancing the silver wire 108. For instance, spool 112 can be mechanically connected to the cover plate 14 so that, whenever the cover plate is moved, the spool 112 will be rotated causing the advance of silver electrode 108. This type of mechanism is well known in the art, and can be, for example, the type of mechanism used to advance film in a camera before each new film exposure. The electrode most consumed is the anode of the generating electrodes. However, it may be desirable to similarly advance other electrodes since they often get coated with protein, etc. Advancing these other electrodes eliminates the need for the operator to cleanse these electrodes. The advancement of the silver electrodes during or after the analysis is, of course, also useful when determining chloride only.

FIG. 4

FIG. 4 shows a portion of the apparatus of FIG. 1, where the tubing 28 connecting the gas space of reaction vessel 10 to detector 30 is modified by the addition of a stainless steel portion 116. Portion 116 of the tubing is connected to an electric heater 118 so that, by heat conduction, portion 116 is elevated in temperature.

It has been found that improved $CO_2$ results are obtained in the combined $CO_2$/$Cl^-$ apparatus described herein when the gas line 28 is heated to about 550° C. This insures that gases having thermal conductivities similar to $CO_2$ will not get to the detector 30 to alter the $CO_2$ measurement. In particular, it has been found that heating the gas flow from reaction vessel 10 to detector 30 will remove impurities.

Stainless steel portion of tubing 28 has a length typically of about 1½ inches, although this is not critical. Its inner and outer diameters are approximately the same as those of tubing 28.

While heat conduction between the electric heater 118 and stainless steel portion 116 is used to heat the gas being transferred to detector 30, other means of applying heat to this gas can be envisioned. For instance, a current can be passed through a resistive heating wire located around portion 116.

In the practice of this invention, the $CO_2$ analysis can be performed before the $Cl^-$ titration, or afterwards. Further, the same acid reagent, such as those described, can be used for both the $CO_2$ analysis and the $Cl^-$ analysis.

While it is advantageous to displace the released $CO_2$ from reaction vessel 10 to detector 30 using a displacing liquid comprising the reagent solution, other techniques can be used for transferring the released $CO_2$ to the detector. For example, the gas phase volume in vessel 10 can be mechanically decreased using a plunger which is pushed into the reaction vessel.

In the practice of this invention, it is preferable that the flow of gas is essentially stopped when the detector determines the concentration of the released $CO_2$. However, with the principles of U.S. Pat. No. 3,964,864, the $CO_2$ measurement may be made while the released gas is flowing at a very low rate through the detector, in order to save time. This low rate is typically below 0.1 ml per second. These low flow rates may be tolerated by detector 30, especially if detector 30 is the type which has two sensors (for example the Gow Mac Model 10-953 Thermal Conductivity Detector). This type of detector has two hot-wire filaments where one is used for the $CO_2$ measurement and the other is used for a reference. By exposing both filaments to the same flow rate (but only one side to the $CO_2$), the effect of flow on the detector is cancelled and measurements may be made even though the sample in the detector is not fully stationary.

While less preferable, the $CO_2$ measurement may be made in other ways known in the art. For example, the signal from detector 30 may be integrated while the $CO_2$ containing gas is flowing through the detector 30. However, it should be kept in mind that a primary advantage of the present invention, i.e., the absence of column separating zones, is still preserved. For this reason and others, high speed measurements can be made.

In the practice of the present invention, several improvements have been made which significantly enhance $CO_2$ and $Cl^-$ detection using the basic principles of U.S. Pat. No. 3,964,864. Among these is the feature that the flushing fluid is in contact with a liquid used in the measurement process. In the examples illustrated, the contacted liquid was illustratively the solution comprising the spent sample and the reagent, while in another example the contacted liquid was the reagent. It will be obvious to one of skill in the art that alternatives to those shown can be used to practice these improvements. For example, numerous reagents may be suitable for the determination of both $CO_2$ and $CL^-$. Further, various techniques for incorporating electrodes in the reaction chamber 10 for titration of $Cl^-$ can be envisioned. Applicant is teaching the advance of the consumable electrode(s) through the chamber of this apparatus in order to provide improved titration and to eliminate maintenance. This, coupled with heating of the gas flow between reaction vessel 10 and detector 30, provides an efficient $CO_2/Cl^-$ analyzer.

What is claimed is:

1. A method for measuring $CO_2$ and chlorides in a sample of body fluid, comprising the steps of:

reacting said sample and a reagent in a vessel to release $CO_2$ into a gas space filled substantially with air at essentially atmospheric pressure to produce a mixture of said released $CO_2$ and air, said gas space having a volume greater than the volume of sample in said vessel, transferring at least a portion of said mixture in said gas space to a detector by adding a displacing liquid to said vessel, measuring the concentration of said transferred gas mixture in said detector, and coulometrically titrating said sample and reagent in said vessel to determine chloride concentration in said sample.

2. The method of claim 1, where said displacing liquid is comprised of said reagent.

3. The method of claim 1, where said detector measures a substantially stationary sample of said transferred gas mixture.

4. The method of claim 1, including the further steps of draining said sample and reagent from said vessel after the concentrations of $CO_2$ and chloride have been determined, and then flushing said detector and said vessel with air which moves in a direction reverse to the direction of transfer of said gas mixture, where said flushing air has been in contact with a liquid present during said method for measuring $CO_2$.

5. The method of claim 3, where said detector measures the thermal conductivity of said transferred gas mixture.

6. The method of claim 1, where said body fluid is comprised of one of the group consisting essentially of whole blood, blood serum, and blood plasma.

7. The method of claim 1, where said transferred mixture is heated to a temperature sufficient to remove impurities therefrom which might adversely affect said $CO_2$ measurement.

8. A method for measuring $CO_2$ and chlorides in a sample of body fluid, comprising the steps of:

reacting said sample and a reagent is a vessel to release $CO_2$ from said sample into a gas space filled substantially with air to produce a mixture of said released $CO_2$ and air, said gas space having a volume greater than the volume of sample in said vessel, transferring at least a portion of said gas mixture in said gas space to a detector, said gas mixture being heated while it is being transferred to said detector, measuring a substantially stationary sample of said transferred gas mixture in a thermal conductivity detector, coulometrically titrating said sample and reagent in said vessel to determine chloride concentration in said sample.

9. The method of claim 8, including the further steps of draining said sample and reagent from said vessel after said concentrations of $CO_2$ and chlorides have been determined and then flushing said detector and said vessel with air which moves in a direction reverse to the direction of transfer of said gas mixture from said gas space to said detector, where said flushing air was in contact with a liquid present in said method for measuring $CO_2$.

10. The method of claim 8, where said gas mixture is heated to at least about 300° C, during said transfer to said detector.

11. A method for measuring $CO_2$ in a sample of body fluid, comprising the steps of:

reacting said sample and a reagent in a vessel to release $CO_2$ into a gas space filled substantially with air to produce a mixture of said released $CO_2$ and air, transferring at least a portion of said gas mixture in said gas space to a detector, measuring the concentration of said transferred gas mixture in said detector, draining said sample and said reagent from said vessel, and flushing said detector and said vessel after said measurement with air which moves through said detector in a direction reverse to the direction of transfer of said gas mixture from said gas space to said detector, said air for flushing having been in contact with a liquid present in said method and beng comprised of vapor constituents which are present in said gas mixture transferred to said detector.

12. The method of claim 11, where said air for flushing has been in contact with a source of water vapor before being used to flush said detector and said vessel.

13. The method of claim 11, where said air for flushing has been in contact with the spent sample and reagent which are drained from said vessel.

14. The method of claim 11, where said air for flushing has been in contact with said reagent.

15. The method of claim 11, where said air to said gas space of said vessel is at substantially atmospheric pressure.

16. The method of claim 11, where said gas mixture is transferred to said detector by adding a displacing fluid to said vessel.

17. The method of claim 11, where said transferred gas mixture in said detector is substantially stationary, at the time of measurement.

18. The method of claim 11, where said body fluid is selected from the group consisting essentially of whole blood, blood serum, and blood plasma.

19. A method for measuring $CO_2$ and chlorides in a sample of body fluid, comprising the steps of:

reacting said sample and a reagent in a vessel to release $CO_2$ into a gas space filled substantially with air to produce a mixture of said released $CO_2$ and air, transferring at least a portion of said mixture in said gas space to a detector, said mixture being heated before said mixture reaches said detector, thermally detecting $CO_2$ in a substantially stationary sample of $CO_2$ and air in said detector, and coulometrically determining the concentration of chlorides in said sample while said sample is in said vessel.

20. The method of claim 19, including the further steps of draining said sample and said reagent from said vessel and flushing said detector and vessel with a flushing fluid which has been in contact with a liquid solution present during said method.

21. The method of claim 20, where said liquid solution is the solution containing the sample and reagent drained from said vessel.

22. The method of claim 20, where said flushing fluid contains water vapor.

23. A method for detection of a species in a sample of body fluid, comprising the steps of:

placing said sample and a reagent in a vessel having a gas space with a given gas mixture therein to react said sample and said reagent to alter the composition of said given gas mixture, transferring at least a portion of said altered gas mixture to a detector by adding a displacing liquid to said vessel, measuring a substantially stationary sample of said altered gas mixture in said detector, draining said sample and reagent from said vessel, and flushing said detector and said vessel with a flushing fluid which moves in a direction reverse to the direction of transfer of said altered gas mixture from said gas space to said detector, where said flushing fluid was in contact with a liquid present during said method.

24. The method of claim 23, where said liquid in contact with said flushing fluid is the sample and reagent drained from said vessel.

25. A method for measuring $CO_2$ and chloride in a sample of body fluid, comprising the steps of:

reacting said sample and a reagent in a vessel to release $CO_2$ from said sample into a gas space having a given gas therein to produce a mixture of said released $CO_2$ and said given gas, transferrng at least a portion of said gas mixture in said gas space to a thermal conductivity detector, measuring a substantially stationary sample of said transferred gas mixture in said detector, and coulometrically titrating said sample and reagent in said vessel to determine the concentration of chloride in said sample.

26. The method of claim 25, where said portion of said transferred gas mixture is heated to remove impurities therefrom which would adversely effect said $CO_2$ measurement.

27. The method of claim 26, including the further steps of draining said sample and reagent from said vessel and flushing said detector and said vessel with a flushing fluid comprised of some of the constituents transferred to said detector during said $CO_2$ measurement, said flushing fluid having been in contact with a liquid present in said method for measuring $CO_2$.

28. The method of claim 27, where said portion of said gas mixture is transferred to said detector by adding additional reagent to said vessel.

29. The method of claim 25, where said coulometric titration uses a plurality of electrodes which enter said vessel and are immersed in the solution of body fluid sample and reagent therein, the method including the further step of advancing at least one of said electrodes so that a previously unused portion of it is immersed in another solution of body fluid sample and reagent placed in said vessel for coulometric titration.

30. The method of claim 25, where said coulometric titration uses a plurality of electrodes which enter said vessel and are immersed in the solution of body fluid sample and reagent therein, the method including the further step of advancing at least one of said electrodes so that a previously unused portion of it is immersed in said solution in said vessel.

31. The method of claim 29, where said electrode that is advanced is a silver wire on a spool which is moved to advance said wire through said vessel to expose previously unexposed portions of it to a solution of reagent and body fluid sample in said vessel.

32. The method of claim 30, where said electrode that is advanced is a silver wire on a spool which is moved to advance said wire through said vessel to expose previously unexposed portions of it to a solution of reagent and body fluid sample in said vessel.

33. A method for detection of a species in a sample of fluid, comprising the steps of:

placing said sample and a reagent in a vessel having a gas space with a given gas mixture therein to react said sample and said reagent to alter the composition of said given gas mixture, transferring at least a portion of said altered gas mixture to a detector by adding a displacing liquid to said vessel, measuring a substantially stationary sample of said altered gas mixture in said detector, draining said sample and reagent from said vessel, and flushing said detector and said vessel with a flushing fluid comprised of the vapors of said altered gas mixture transferred to said detector, said flushing fluid having been in contact with a liquid used in said method.

34. The method of claim 33, where said flushing fluid contains water vapor.

35. The method of claim 33, including the step of coulometrically titrating the solution of said sample and reagent in said vessel to determine the chloride concentration in said sample.

36. The method of claim 35, where said titration is achieved using a plurality of electrodes in said solution of sample and reagent in said vessel, at least one of said electrodes being moved so that a new portion of it is exposed to said solution when another sample is to be coulometrically titrated in said vessel.

37. A method for coulometric titration of a sample of body fluid to determine chloride concentration therein, including the steps of:

passing current between electrodes immersed in a sample of said body fluid to release silver ions into said sample where they combine with chlorides present therein, and detecting the presence of excess silver ions in said sample, wherein at least one of said electrodes is advanced so that a new portion of said advanced electrode is exposed to said sample.

38. An apparatus for coulometric titration of chloride in a sample of body fluid, comprising:

a vessel in which a solution comprising said sample and a reagent is contained, a plurality of electrodes which enter said vessel and are immersed in said solution, means for passing current through at least some of said electrodes to release ions into said solution which combine with chloride present therein, said some electrodes having portions thereof which are not immersed in said solution, means for advancing said electrodes to immerse said previously unimmersed portions in a solution of another sample and reagent put into said vessel for coulometric titration thereof.

39. A method for measuring $CO_2$ in a sample of body fluid, comprising the steps of:

reacting said sample and a reagent in a vessel to release $CO_2$ into a gas space filled substantially with air to produce a mixture of said released $CO_2$ and air, transferring at least a portion of said gas mixture in said gas space to a detector, measuring the concentration of said transferred gas mixture in said detector, draining said sample and said reagent from said vessel, and flushing said detector and said vessel after said measurement with air which moves through said detector in a direction reverse to the direction of transfer of said gas mixture from said gas space to said detector, said air for flushing having substantially the same constituents therein as said gas mixture transferred to said detector, except that $CO_2$ is essentially absent in said air for flushing.

* * * * *

UNITED STATES PATENT AND TRADEMARK OFFICE
CERTIFICATE OF CORRECTION

PATENT NO. : 4,019,861
DATED : April 26, 1977
INVENTOR(S) : Harald Dahms

It is certified that error appears in the above-identified patent and that said Letters Patent are hereby corrected as shown below:

Column 2, line 47, "($Ag^{115}$)." should be -- ($Ag^+$). --.

Column 10, line 40, "preparation" should be -- operation --.

Column 15, line 22, Claim 15, "to" should be -- in --.

Signed and Sealed this thirtieth Day of August 1977

[SEAL]

Attest:

RUTH C. MASON
Attesting Officer

C. MARSHALL DANN
Commissioner of Patents and Trademarks